United States Patent [19]

Kotani et al.

[11] Patent Number: 5,648,251

[45] Date of Patent: Jul. 15, 1997

[54] METHOD OF TRANSDUCTION OF CELLS WITH RETROVIRAL VECTORS

[75] Inventors: Hitoshi Kotani, Middletown; Perry Newton, III, Odenton; Shuyuan Zhang, Gaithersburg, all of Md.

[73] Assignee: Genetic Therapy, Inc., Gaithersburg, Md.

[21] Appl. No.: 450,914

[22] Filed: May 26, 1995

Related U.S. Application Data

[62] Division of Ser. No. 180,717, Jan. 12, 1994, abandoned.

[51] Int. Cl.$^6$ .............................. C12N 5/10; C12N 15/64
[52] U.S. Cl. ........................................................ 435/172.3
[58] Field of Search ........................... 435/172.3, 5, 69.1

[56] References Cited

U.S. PATENT DOCUMENTS

| | | | |
|---|---|---|---|
| 4,753,884 | 6/1988 | Kit et al. | 424/205.1 |
| 4,992,051 | 2/1991 | Kit et al. | 435/235.1 |
| 5,075,110 | 12/1991 | Francon et al. | 424/202.1 |

OTHER PUBLICATIONS

David A. Williams, "Expression of Introduced Genetic Sequences in Hemotopoietic Cells Following Retroviral–Mediated Gene Transfer" Human Gene Therapy, vol. 1, pp. 229–239, 1990.

Fred D. Ledlez, "Clinical Considerations in the Design of Protocols for Somatic Gene Therapy", Human Gene Therapy, vol 2, pp. 77–83, 1991.

Kotane et al., "Improved Methods of Retroviral Vector Transduction and Production of Gene Therapy", Human Gene Therapy, vol. 5, pp. 19–28, 1994.

Syrewicz, et al., Applied Microbiology, vol. 24, No. 3, pp. 488–494 (Sep. 1972).

Moennig, et al., Virology, vol. 61, pp. 100–110 (1974).

Bodine, et al., Proc. Nat. Acad. Sci., vol. 87, pp. 3738–3742 (May 1990).

Rousculp, et al., Human Gene Therapy, vol. 3, pp. 471–477 (1992).

Paul, et al., Human Gene Therapy, vol. 4, pp. 609–615 (1993).

Primary Examiner—David Guzo
Attorney, Agent, or Firm—Elliot M. Olstein; Raymond J. Lillie

[57] ABSTRACT

The present invention relates to an efficient method, termed spin transduction, of transducing cells with retroviral vectors. Retroviral particles, suspended in a pharmaceutically acceptable carrier, are contacted with the cells to be transduced, and the mixture is centrifuged for a sufficient period of time to permit transduction. This method leads to a 3- to 15-fold increase in transduction efficiency, depending on the type of cells transduced.

10 Claims, 3 Drawing Sheets

METHOD OF TRANSDUCTION OF CELLS WITH RETROVIRAL VECTORS

This is a Division of application Ser. No. 08/180,717 filed Jan. 12, 1994.

This invention relates to the purification of retroviral vectors. More particularly, this invention relates to a method of large scale purification of retroviral vector particles whereby one obtains improved recovery of retroviral vector particles from a culture of retroviral vector producer cells.

The number of human trials in human gene therapy continues to increase. In addition, preclinical studies in new approaches directed to human gene transfer similarly have increased. While several gene delivery systems with adenoviral vectors and liposomes have been studied, at present, the retroviral vector systems account for the overwhelming number of published reports and human trials (Miller, et al., *Mol. Cell. Biol.*, Vol. 6, pgs. 2895-2902 (1986); Danos, et al., *PNAS*, Vol. 85, pgs. 6460-6464 (1988). Muenchau, et al., *Virology*, Vol. 176, pgs. 262-265 (1990); Miller, *Curr. Top. Microbiol. Immunol.*, Vol. 158, pgs. 1-24 (1992)). To date, the diseases under investigation involving the use of retroviral vectors for gene therapy include various types of cancer, genetic diseases (including adenosine deaminase deficiency, cystic fibrosis, and familial hypercholesteremia), and infectious diseases, specifically AIDS (Rosenberg et al., *N. Engl. J. Med.*, Vol. 323, pgs. 570-578 (1990); Anderson, et al., *Hum. Gene. Ther.*, Vol. 1, pgs. 331-362 (1990); Grossman, et al., *J. Lab. Clin. Med.*, Vol. 119, pgs. 457-460 (1992); Riddel, et al., *Hum. Gene, Ther.*, Vol. 3, pgs. 319-338 (1992)). At present, human trials are Phase I and/or II clinical trials to insure safety of the delivery system and the specific transgene. These early trials may also generate some meaningful information on efficacy.

In order to facilitate clinical applications of retroviral-mediated human gene transfer, retroviral vectors must be of high titer and free of detectable replication-competent retroviruses. However, it has been difficult to obtain large quantities of such retroviral vectors.

Figure 1:
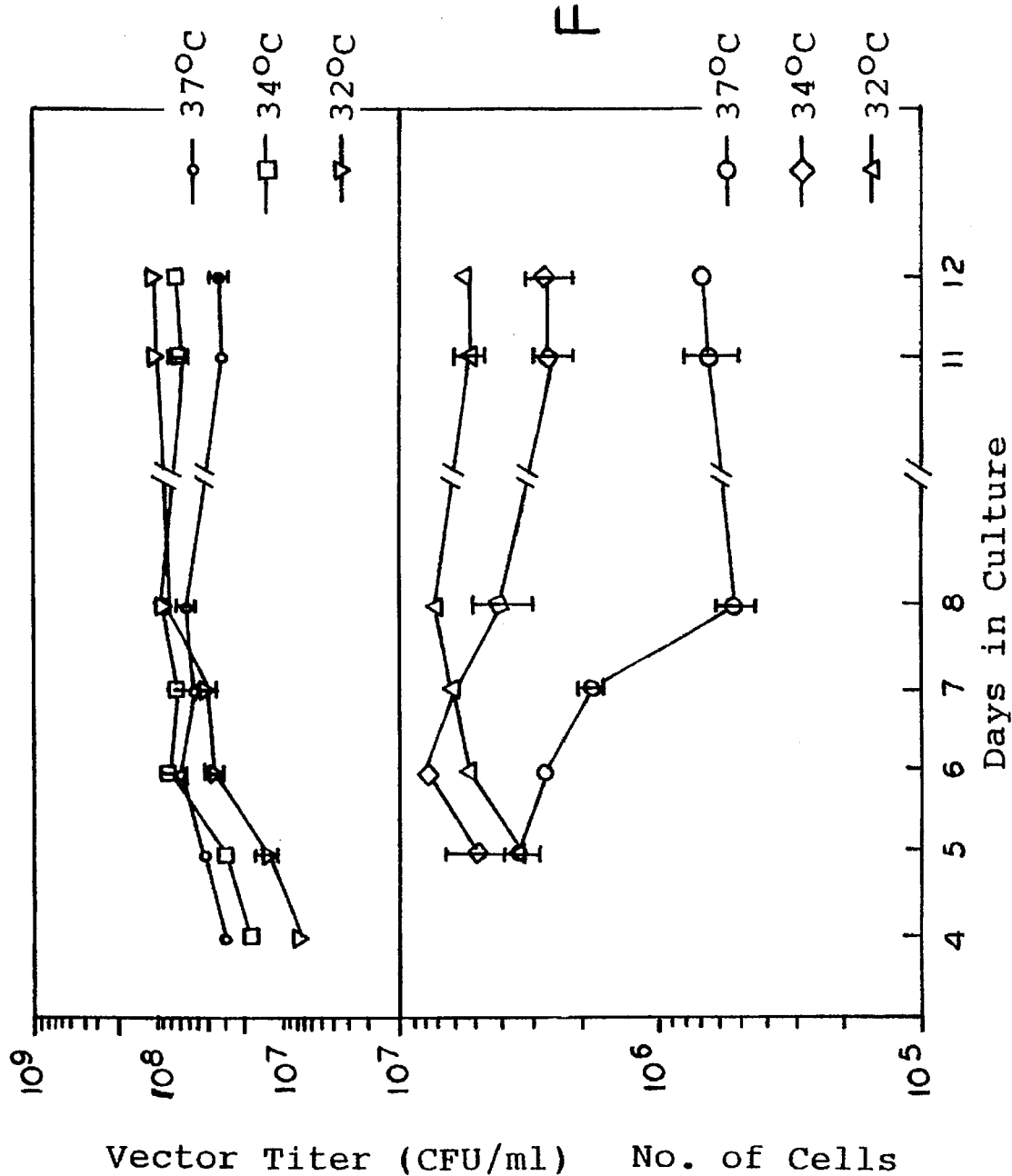
FIG. 1. Number of cells and vector titers of PA317/G1Na.40 producer cells grown in 75-cm$^2$ flasks at different temperatures.

It is an object of the present invention to provide a method for purifying retroviral vector particles whereby one obtains an increased amount of retroviral vector particles.

In accordance with an aspect of the present invention, there is provided a method of purifying retroviral vector particles. The method comprises culturing retroviral vector producer cells, which are capable of generating retroviral vector particles. A supernatant containing retroviral vector particles then is obtained from the culture of retroviral vector producer cells. The supernatant then is clarified, and then the clarified supernatant is concentrated after clarification. The concentrated supernatant then is contacted with a precipitation agent to form a precipitate containing the retroviral vector particles. The precipitate is recovered, and the recovered precipitate is suspended in a liquid. The retroviral vector particles are separated from the remainder of the precipitate by density gradient centrifugation. The separated retroviral vector particles then are recovered.

The above method enables one to obtain purified retroviral vector particles. The term "purified retroviral vectors particles" as used herein means a preparation of retroviral particles containing at least 80% by weight, preferably at least 85% by weight, and more preferably at least 90% by weight, of retroviral vector particles.

The retroviral vector producer cells may be cultured in any of a variety of monolayer culture systems. Such producer cells may be cultured in T-flasks, roller bottles, or bioreactors. The cells may be cultured in any acceptable culture medium such as, for example, AIM-V medium (Gibco BRL, Grand Island, N.Y.) containing 5% fetal bovine serum, or Dulbecco's modified Eagle medium (DMEM) with high glucose (4.5 g/l) supplemented with 10% heat-inactivated fetal bovine serum.

The producer cell line may be formed by transducing an appropriate packaging cell line with retroviral vectors. Examples of packaging cell lines which may be transduced include, but are not limited to, the PA317, PE501, Ψ-2, Ψ-AM, PA12, T19-14X, VT-19-17-H2, ΨRE, ΨCRIP, GPL, GP+E-86, GP+envAm12, and DAN cell lines. The vector may transduce the packaging cells through any means known in the art. Such means include, but are not limited to, electroporation, the use of liposomes, and $CaPO_4$ precipitation.

The cells generally may be cultured at a temperature of from about 32° C. to about 37° C. Most preferably, the cells are cultured at a temperature of about 32° C. At 32° C., the vector particles have a half-life of up to about 48 hours.

The viral supernatant, which is obtained from the culture of retroviral vector producer cells, and which may have a titer of, for example, from about 10$^6$ to about 10$^7$ CFU/ml, may be clarified by passing the supernatant through a filter means, such as a nominal type filter unit. The filter may have a pore size of from about 0.2µ to about 5.0µ, preferably from about 0.8µ to about 1.5µ. Most preferably, the filter has a pore size of about 1.2µ.

The clarified viral supernatant then may be concentrated by passing the clarified viral supernatant through a tangential flow filtration system. Preferably, the membrane in such system has a 300,000 molecular weight cutoff. Such a system may reduce the volume of supernatant containing retroviral vector particles by about 16 to 25 times, with vector recovery being at least 90%. An example of a tangential flow filtration system which may be employed in accordance with the present invention is a Millipore Pellicon tangential flow filtration system (Millipore, Bedford, Mass.) with a PLMK000C5 cassette (5 square feet, 300,000

NMWL). The system also may be equipped with a pump to exert a low membrane feed pressure of 5 psi. Such a concentrated viral supernatant may have a vector recovery of greater than 95% compared with the amount of vector present prior to concentration, and a vector titer of from about $10^7$ to about $10^8$ CFU/ml.

The concentrated viral supernatant then is contacted with a precipitation agent. In one embodiment, the precipitation agent is a polyalkylene glycol, such as, for example, polyethylene glycol. In a preferred embodiment, once the viral supernatant is contacted with the precipitation agent, the viral supernatant and the precipitation agent are centrifuged at a speed of from about 8,000×g to about 10,000×g to pellet precipitated material, which then is recovered. Such precipitate contains the retroviral vector particles. The recovered precipitate is suspended in a liquid, such as a buffer. The retroviral vector particles are separated from the remainder of the precipitate by density gradient centrifugation. Preferably, the suspended precipitate is subjected to sucrose gradient ultracentrifugation (discontinuous or preferably linear). More preferably, the ultracentrifugation is effected at a speed of from about 100,000×g to about 120,000×g. After centrifugation, the retroviral vector particles are recovered. Vector recovery may be greater than 95%, and vector titer may be from about $10^9$ to about $10^{10}$ CFU/ml. An example of purifying viral supernatant by polyethylene glycol precipitation and sucrose gradient centrifugation is described in Syrewicz, et al., *Appl. Microbiol.*, Vol. 24, pgs. 488–494 (1972), incorporated herein by reference.

The above purification steps enable one to recover an increased amount of retroviral vector particles. The resulting preparation containing the retroviral vector particles is free of components which may compete with the retroviral vector particles for binding sites located on target cells to which the retroviral vector particles may bind and infect. Such components include free gp70 protein and empty viral particles.

If desired, the retroviral vector particles recovered from the centrifugation step may be lyophilized and saved for future use. Such lyophilization may be carried out by adding to the retroviral vector supernatant solutions of glucose and/or sorbitol and gelatin in phosphate buffered saline. The samples then maybe frozen in a dry ice/acetone bath and then placed in a freeze dryer. When the retroviral vector particles are needed for gene therapy, the lyophilized retroviral vector particles may be reconstituted by adding an equal volume of sterile water. After reconstitution, vector recovery may be greater than 90%, and vector titer may be from about $10^9$ to about $10^{10}$ CFU/ml.

The purified retroviral vector particles are used to transduce cells in vivo or ex vivo for purposes of gene therapy. For ex vivo transduction, the inventors have developed a novel preferred transduction method, which they call spin transduction. The particles, suspended in a pharmaceutically acceptable carrier, are contacted with the cells to be transduced, and the mixture is centrifuged for a sufficient period of time to permit transduction. The mixture is centrifuged at 1,000–4,000 rpm, preferably at 2,000–3,000 rpm, and most preferably at about 2,500 rpm for a period of time from about 30 minutes to 3 hours, preferably 1 to 2 hours, and most preferably about 90 minutes. The spin transduction is done at a tempreature of 15° C. to 37° C., preferably 20° C. to 35° C., and most preferably 32° C. This method leads to a 3- to 15-fold increase in transduction efficiency, depending on the type of cells transduced.

The invention now will be described with respect to the following example; however, the scope of the present invention is not intended to be limited thereby.

EXAMPLE

Unless noted otherwise, all viral vector titers of retroviral vectors carrying the neomycin resistance marker are determined by a G418 selection method using NIH 3T3 TK-cells as target cells. The assay procedure is as follows:

On day 1, NIH-3T3 TK-cells were seeded at $1 \times 10^5$ cells/well of a six-well tissue culture plate (Becton Dickinson, Lincoln Park, N.J.) and incubated at 37° C. in 5% $CO_2$. On day 2, serial ten-fold dilutions of vector specimen in medium containing 8 µg/ml Polybrene were added to the target cells and incubated at 32° C. for an additional 24 hours. On day 3, the medium was removed and replaced with medium containing 800 µg/ml G418. Plates were incubated at 37° C. in 5% $CO_2$. On day 6, plates were refed with medium containing 800 ug/ml G418. On day 8, colonies were stained with methylene blue and the vector titer was calculated as the number of colony forming units (cfu) per ml.

A. Formation of Producer Cell Lines.

The following producer cell lines were formed by transducing retroviral vectors including various desired genes and promoters (sometime hereinafter referred to as Gene 1, Gene 2, Promoter 1, and Promoter 2) into the PA317 amphotropic retrovirus packaging cell line (Miller, et al, *Mol. Cell. Biol.*, Vol. 6, pgs. 2895–2902 (1986); Miller, et al., *Biotechniques*, Vol 7, pgs. 980–990 (1989), incorporated herein by reference), were formed by standard transduction techniques. The producer cell lines are given in Table I below:

TABLE I

| Producer cells | Gene 1 | Promoter 1 | Gene 2 | Promoter 2 |
|---|---|---|---|---|
| PA317/G1Na.40 | Neo$^R$ | LTR | — | — |
| PA317/G1Na.47 | Neo$^R$ | LTR | — | — |
| PA317/G1IL2RαSvNa.3 | IL-2Rα | LTR | Neo$^R$ | SV40 |
| PA317/G1IL2RβSvNa.14 | IL-2Rβ | LTR | Neo$^R$ | SV40 |
| PA317/G1NaCvI2G | Neo$^R$ | LTR | IL-2 | CMV |
| PA317/G1NaBcI2G.6 | Neo$^R$ | LTR | IL-2 | β-Actin |
| PA317/G1βGsvna.29 | lacZ | LTR | Neo$^R$ | SV40 |
| PA317/G1NaSvnβg.2-1 | Neo$^R$ | LTR | lacZ | SV40 |
| PA317/G1NaSvnβg.2-12 | Neo$^R$ | LTR | lacZ | SV40 |
| PA317/GlnβGsvna.8-1 | lacZ | LTR | Neo$^R$ | SV40 |
| PA317/GlnβGsvna.8-3 | lacZ | LTR | Neo$^R$ | SV40 |
| PA317/G1NaSvAd.24 | Neo$^R$ | LTR | ADA | SV40 |
| PA317/LASN | ADA | LTR | Neo$^R$ | SV40 |
| PA317/G1F1SvNa.19c | IFN-α | LTR | Neo$^R$ | SV40 |
| PA317/G1NaCvF32.20 | Neo$^R$ | LTR | IFN-r | CMV |
| PA317/G1T2SvNa.24 | TNF-α | LTR | Neo$^R$ | SV40 |
| PA317/LT12SN.40 | TNF-α | LTR | Neo$^R$ | SV40 |
| PA317/LNCT11.8 | Neo$^R$ | LTR | TNF-α | CMV |
| PA317/LNST11.20 | Neo$^R$ | LTR | TNF-α | SV40 |
| PA317/G1MD.1-15 | MDR1 | LTR | — | — |
| PA317/G1MD.S-5 | MDR1 | LTR | — | — |
| PA317/LIXSN | Factor IX | LTR | Neo$^R$ | SV40 |

Producer cell line PA317/G1Na.40 is described in Miller, *Curr. Top. Microbiol. Immunol.*, Vol. 158, pgs. 1–24(1992), incorporated herein by reference. Producer cell line PA317/LASN is described in Hock, et al., *Blood*, Vol. 74, pgs. 876–881 (1989), incorporated herein by reference. Producer cell line PA317/L1XSN is described in Palmer, et al., *Blood*, Vol. 73, pgs. 438–445 (1989), incorporated herein by reference.

B. Culturing of Producer Cells

PA317/G1Na.40 producer cells ($2 \times 10^6$ cells) were inoculated in 75-cm$^2$ flasks and were incubated at 37° C., 34° C., and 32° C. in 5% $CO_2$ to determine the effect of incubation temperature on vector titer. The medium was changed every day.

The amphotropic retroviral vectors were assayed by a G418 selection method using NIH-3T3 TK⁻ cells as target cells. On day 1, NIH-3T3 TK⁻ cells were seeded at $1\times10^5$ cells/well of a six-well tissue culture plate (Becton Dickinson, Lincoln Park, N.J.) and incubated at 37° C. in 5% $CO_2$. On day 2, serial ten-fold dilutions of vector specimen in medium containing 8 µg/ml Polybrene were added to the target cells and incubated at 32° C. for an additional 24 hr. On day 3, the medium was removed and replaced with medium containing 800 µg/ml G418. Plates were incubated at 37° C. in 5% $CO_2$. On day 6, plates were refed with medium containing 800 µg/ml G418. On day 8, colonies were stained with methylene blue and the vector titer was calculated as the number of colony forming units (cfu) per ml.

The results are shown in FIG. 1. Cells grown at 37° C., 34° C., and 32° C. achieved 100% confluence on days 5, 6, and 8, respectively. Days 5, 6, and 8 also showed the highest vector titers for each of the three temperatures. Retroviral vector titers increased as temperature decreased. The highest vector titer of 1-day-old supernatant was always obtained from cells incubated at 32° C., $8.5\times10^6$ cfu/ml, and remained at that approximate level for 5 days. Cells incubated at 37° C. showed the lowest titer over 7 days. In the experiment shown in FIG. 1, the maximum titer difference between 32° C. and 37° C. was 1.5 logs on day 8. Vector from cells incubated at 34° C. yielded titers intermediate between 32° C. and 37° C. Interestingly, the highest number of cells ($1.1\times10^6$) was obtained at 32° C. on day 12. During the experiment, viability of the cells for each temperature ranged between 92 and 98%.

Figure 2:
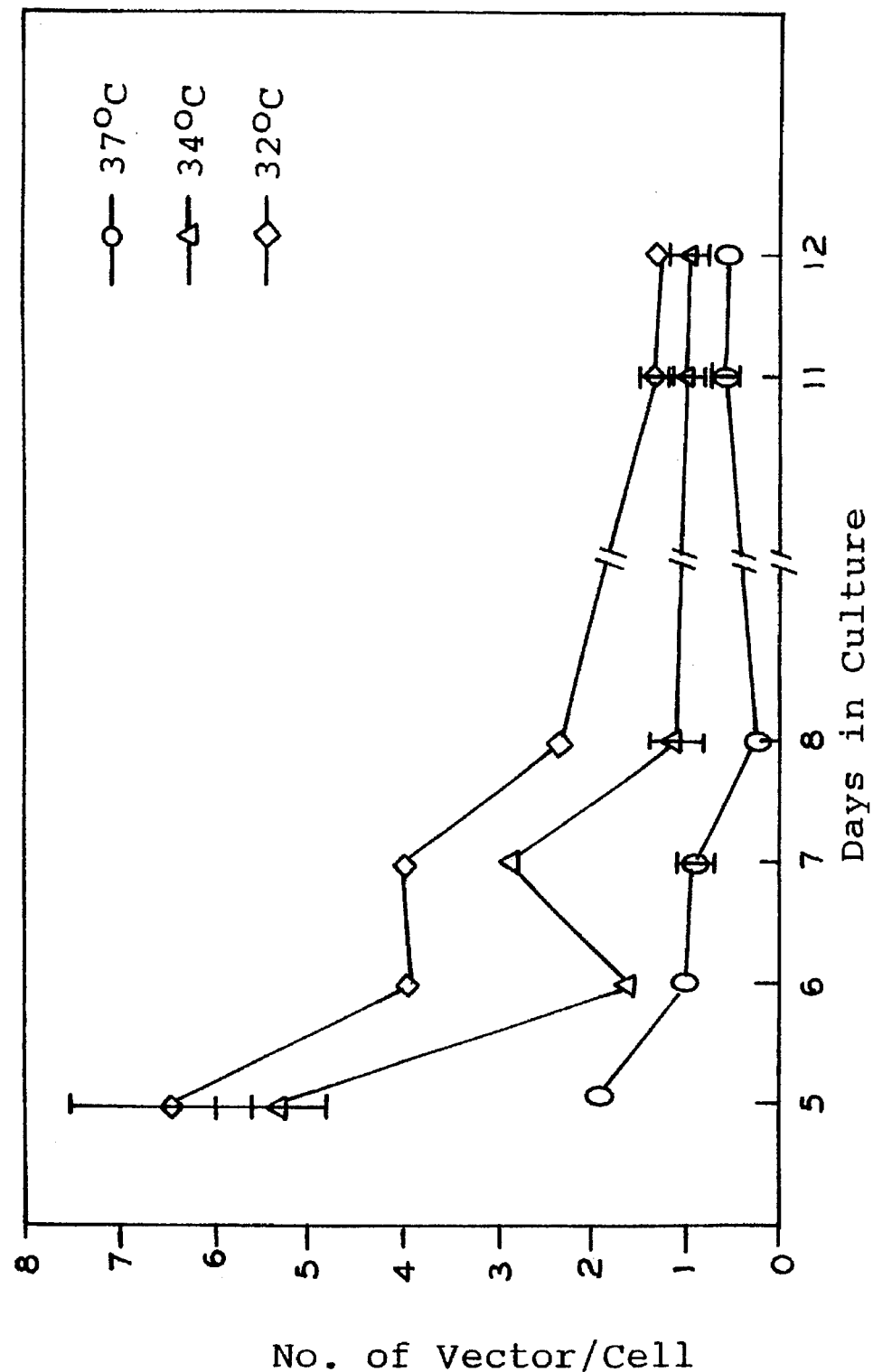
FIG. 2. Effect of temperature on viral particles per cell during 12 days of culture. PA317/G1Na.40 producer cells were grown in 75-cm$^2$ flasks at 37 C., 34 C. and 32 C. Medium was changed every 24 hr. Cell number and vector titer were determined daily.

The number of vector particles per cell was calculated by dividing the number of vector particles per milliliter determined in a standard titer assay by the number of cells from viability counts. As shown in FIG. 2, the 32° C. and 34° C. incubation temperatures showed a maximum of six vector particles per cell compared with a maximum of two vector particles per cell at 37° C. under the conditions of these calculations.

To determine the effect of $CO_2$ on production of viral vectors, PA317/G1Na.40 cells were grown in 75-cm² flasks and roller bottles with and without 5% $CO_2$ in air. The titer of vector supernatants cultivated under both conditions revealed similar titers at the three incubation temperatures studied (data not shown). The results of these studies and those with other vectors suggest that endogenous $CO_2$ from the cells support the cell growth and vector production without 5% exogenous $CO_2$.

Producer cells were easily adapted to grow in 850-cm² roller bottles. Cells maintained maximum confluence for at least 2 weeks. PA317/G1Na.40 and PA317/LT12SN.40 producer cells were grown in roller bottles and incubated at 37° C., 34° C., and 32° C. After the cells reached confluence, the medium was harvested daily. The vector titers shown in Table II below represent the titers reached after 100% confluence.

TABLE II

Vector Titers from Cells Grown in Roller Bottles (850 cm²) at 37° C., 34° C., and 32° C.

| Vector | Temperature | | |
|---|---|---|---|
| | 37° C. | 34° C. | 32° C. |
| PA317/G1Na.40 | $2.9\times10^{6b}$ | $4.7\times10^6$ | $1.7\times10^7$ |
| | ($\pm 1\times10^6$)ᵃ | ($\pm 1.4\times10^5$) | ($\pm 2.1\times10^6$) |
| PA317/LT12SN.40 | $2.3\times10^6$ | $1.2\times10^7$ | $1.8\times10^7$ |
| | ($\pm 1\times10^5$) | ($\pm 2.0\times10^6$) | ($\pm 3.3\times10^6$) |

ᵃProducer cells ($2\times10^7$) were seeded in roller bottles and incubated at 37° C., 34° C., and 32° C. The supernatant from producer cells were harvested after 100% confluence.
ᵇVector titer in 1-day-old supernatant.

The titers from each temperature remained stable without significant change for the 2-week experimental time period. A significant increase of vector titer was achieved at 32° C. incubation temperature. The titer of PA317/G1Na.40 increased from $2.9\times10^6$ cfu/ml at 37° C. to $1.7\times10^7$ cfu/ml at 32° C. A significant increase in titer also was achieved with vector PA317/LT12SN.40, $2.3\times10^6$ cfu/ml at 37° C. to $1.8\times10^7$ cfu/ml at 32° C. The results of increased vector titer at 32° C. compared to 37° C. incubation for both 75-cm² flasks (FIG. 1) and roller bottles (Table II) are statistically significant at the $p<0.01$ probability level.

Supernatants from PA317/G1Na.40 and PA317/LT12SN.40 producer cells grown in roller bottles were collected at 1- and 2-day intervals at 32° C. cultivation (Table III).

TABLE III

Vector Titers in 1-Day- and 2-Day-Old Supernatants in Roller Bottles

| Vector | 1-Day-Old Supernatant | 2-Day-Old Supernatant |
|---|---|---|
| PA317/G1Na.40 | $1.1\times10^{7b}$ | $2.1\times10^7$ |
| | ($\pm 4.5\times10^6$)ᵃ | ($\pm 4.9\times10^6$) |
| PA317/LT12SN.40 | $3.1\times10^6$ | $1.2\times10^7$ |
| | ($\pm 1.5\times10^5$) | ($\pm 1.5\times10^6$) |

ᵃProducer cells were grown in roller bottle at 32° C. The supernatants from producer cells were harvested at 100% cell confluence.
ᵇVector titer (CFU/ml).

The vector titer of 2-day-old supernatants from PA317/G1Na.40 and PA317/LT12SN.40 were approximately two times and four times higher than that of 1-day-old supernatants, respectively. The above results from 2-day-old supernatant collection at 32° C. incubation also were demonstrated using several of the other producer cell lines. Increased titers at lower temperature may be partially due to decreased vector inactivation at the lower temperature.

Roller bottles of different surface areas were compared for vector yield. As expected, the vector titer from supernatants of PA317/G1Na.40 and PA317/G1βGsvna.29 producer cell lines from a pleated roller bottle of 1,700-cm² surface area were approximately twice that of the 850-cm² roller bottle (Table IV).

TABLE IV

Vector Titers in Supernatants from Cells Grown in Different Types of Roller Bottles at 32° C.

| Vector | Type of Roller Bottle | |
|---|---|---|
| | 850 cm² | 1,700 cm² |
| PA317/G1Na.40 | $1.2 \times 10^{7b}$ | $2.6 \times 10^7$ |
| | $(\pm 3.5 \times 10^6)^a$ | $(\pm 4.3 \times 10^6)$ |
| PA317/G1BgSvNa.29 | $4.2 \times 10^6$ | $1.0 \times 10^7$ |
| | $(\pm 6.0 \times 10^5)$ | $(\pm 3.5 \times 10^6)$ |

[a]Producer cells were grown in roller bottles at 32° C. Two-day-old supernatants were collected after 100% cell confluence.
[b]Vector titer (CFU/ml).

The number of cells counted at the end of the 2-week culture from a 1,700-cm² roller bottle was approximately twice that counted from the 850-cm² roller bottle (data not shown), suggesting that the vector yield per cell did not differ in the pleated and unpleated bottles. To date, the highest virus titer achieved was from a 2-day-old PA317/G1Na.40 supernatant from the pleated-type roller bottle incubated at 32° C., $1 \times 10^6$ cfu/ml. This has been repeated two times. Twenty-one of 22 different retroviral vector producer cells increased titers by a 2-day-old supernatant at 32° C. incubation. Vector LASN was the exception in this study.

C. Clarification of Viral Supernatant

The viral supernatant was harvested from the roller bottle by aspiration or pouring into a collection bottle. Immediately thereafter, the supernatant was clarified by pumping the supernatant through a 1.2μ nominal type polypropylene filter (Sartorius) to remove any debris and cells.

D. Concentration of Vector Supernatant

Vector supernatants from PA317/G1Na.40, PA317/LT12SN.40, and PA317/G1NaSvAd.24 producer cells were concentrated using the Millipore Pellicon tangential flow filtration system (Millipore, Bedford, Mass.) with a PLMK000C5 cassette (5 square feet, 300,000 NMWL). A pump was used to exert a low membrane feed pressure of 5 psi. Concentration was achieved within 30 minutes. To ensure high vector recovery, it is necessary to maximize the surface area of the membrane and minimize supernatant circulation with a low membrane feed pressure. As shown in Table V below, the volume of the supernatant was reduced from 16 to 25 times, and the vector titer increased from 15 to 24 times. Vector recovery ranged from 91% to 96%.

E. Centrifugation of Vital Supernatant and Recovery of Retroviral Vectors Therefrom The concentrated viral supernatant (from about 100 ml to about 200 ml) was mixed with a 1/10 volume of 4M NaCl on ice while stirring. Polyethylene glycol was added (8% w/v) slowly and stirred in ice for 3 hours. The precipitate was collected by centrifugation at 8,000×g for 15 minutes and resuspended in 0.01M tris (hydroxymethyl) aminomethane hydrochloride (TNE) pH7.5, 0.1M NaCl, and 0.001M ethylenediamine tetracetic acid (i.e., at from about 1/100 to 1/25 of the original supernatant volume).

The suspension was layered on a discontinuous sucrose gradient (20% and 55% w/w) in TNE and centrifuged in a Beckman SW-40Ti rotor at 100,000×g for 2 hours at 4° C.

After the centrifugation, the sharp virus band was observed. The virus band was collected by inserting a 21-gauge hypodermic needle into the centrifuge tube, and diluted ten-fold with TNE and stored at −70° C. Vector recovery was greater than 95% and vector titer was at least $10^9$ CFU/ml.

F. Lyophilization of Retroviral Vectors

Lyophilization of retroviral vectors was performed using a Model Freeze Mobil Lyophilizer (Virtis, Gardiner, N.Y.). The additives, glucose, sorbitol, and gelatin, were prepared as 50%, 50%, and 25% solutions, respectively, in phosphate-buffered saline (PBS). The solutions were filtered through 0.22 μm filters. Aliquots of glucose (1 ml), sorbitol (1 ml), or sorbitol with gelatin (1 ml) were added to the viral supernatant (19 ml) derived from PA317/G1Na.40 producer cells. The samples were frozen quickly in 1.0 ml or 20 ml aliquots in a dry ice/acetone bath and placed in a freeze-dryer. The lyophilized material was stored at 4° C. Samples were reconstituted with an equal volume of sterile water.

Retroviral vectors were preserved after lyophilization and retained relatively high transducibility. As shown in Table VI below, samples without additives showed the lowest recovery rate, 21%. Specimens supplemented with glucose, sorbitol, or gelatin demonstrated a relatively low recovery rate (from 48% to 61%). The combination of glucose or sorbitol with gelatin, however, demonstrated a higher vector recovery rate (from 64% to 83%). The viral titer was from $2 \times 10^6$ cfu/ml to $3 \times 10^6$ cfu/ml after lyophilization.

TABLE V

| Vector | Volume of supernatant (ml) | | | Titer (cfu/ml) | | Vector concen. | Vector recovery |
|---|---|---|---|---|---|---|---|
| | Before conc. | After conc. | Volume reduction | Before conc. | After conc. | | |
| PA317/G1Na.40 | 10,000 | 400 | 25X | $1.7 \times 10^6$ | $4.1 \times 10^7$ | 24X | 96% |
| PA317/LT12SN.40 | 10,000 | 500 | 20X | $2.5 \times 10^6$ | $4.5 \times 10^7$ | 18X | 91% |
| PA317/G1NaSvAd.24 | 8,000 | 500 | 16X | $1.6 \times 10^6$ | $2.4 \times 10^7$ | 15x | 94% |

TABLE VI

Recovery of PA317/G1Na.40 Vector After Lyophilization

| Additive | Virus Recovery |
|---|---|
| None | 21% |
| 5% Glucose | 61% |
| 5% Sorbitol | 58% |
| 2.5% Gelatin | 48% |
| 5% Glucose/2.5% Gelatin | 64% |
| 5% Sorbitol/2.5% Gelatin | 65% |
| 5% Glucose/5% Sorbitol/2.5% Gelatin | 83% |

G. Transduction of Cells with Recovered Vector Supernatant

NIH3T3 TK⁻ cells were seeded at $1 \times 10^5$ cells/well in a six-well plate as an adherent target cell line and incubated at 37° C. overnight to yield approximately a 60% confluent monolayer. A 10-fold serial dilution of vector supernatants ($10^{-4}$, $10^{-5}$, and $10^{-6}$) containing 8 µg/ml Polybrene were added in duplicate to appropriate wells on day 2. The six-well plate was centrifuged at 2,500 rpm for 90 min. at 32° C. by using a plate holder in a Beckman GS-6KR centrifuge (Beckman, Fullerton, Calif.). After centrifugation, the plate was incubated at 32° C. overnight. On day 3, the wells were refed with 5 ml of medium containing 800 µg/ml G418. The plate was incubated at 37° C. for 3 days. On day 5, medium was replaced to remove dead cells. On day 8, G418-resistant colonies were stained and counted.

In additional experiments, HUT 78 cells, a human T-cell leukemia line, as a suspension target cell line, were transduced with an amphotrophic vector PA317/G1MD1-15 which carried the MDR1 gene encoding p-glycoprotein (Endicott, et al., Ann. Rev. Biochem., Vol. 58, pgs 137–171 (1989)).

Cells were seeded at $1 \times 10^6$ cells/well of a 24-well plate (Costar, Cambridge, Mass.). A higher number of HUT 78 cells were needed to cover the bottom of the well. Two milliliters of vector supernatant containing 8 µg/ml of Polybrene was added to each well. The plate was centrifuged at 2,500 rpm for 90 min. at 32° C. and incubated at 32° C. overnight. The next day the wells were refed with fresh medium and incubated at 37° C. for 3 days. Cells were collected and washed two times with Hank's balanced salt solution (HBSS) and assayed for rhodamine afflux pump by FACS analysis and for the MDR1 gene by polymerase chain reaction (PCR) assay. As a control, untransduced HUT 78 cells were assayed.

FACS analysis was performed to determine transduction of HUT 78 cells with vector (PA317/G1MD.1-15) by a modification of the method described previously (Kessel et al., Cancer Res., Vol. 51, pgs. 4665–4670 (1991)). Cells were incubated at 37° C. for 20 min. then centrifuged at 1,500 rpm for 10 min. Cells were resuspended in basal medium and affluxed at 37° C. for 45 min. Cells were centrifuged and resuspended in HBSS ($1 \times 10^4$ cells/ml). Flow cytometry was performed using an EPICS C Cytometer (Coulter, Hialeah, Fla.).

The PCR was employed to screen for the presence of the G1MD1 retroviral sequence in HUT 78 cells after transduction. Genomic DNAs from cells subjected to G1MD1 transduction as well as untransduced cells were isolated using the Elu-Quik system (Schleicher & Schuell, Keene, N.H.). Each 100 µl reaction included 1 µg of genomic DNA using standard reaction conditions: 1.5 mM $MgCl_2$, 0.2 mM dATP, 0.2 mM dGTP, 0.2 mM dCTP, 0.2 mM TTP, 50 mM KCl, 10 mM Tris-HCl, pH 7.3, 1 µM synthetic primers (MDR1), 0.01 units/µl Perfect Match Polymerase Enhancer (Strategene, La Jolla, Calif.), and 0.025 units/µl AmpliTaq DNA polymerase (Perkin-Elmer Cetus, Emeryville, Calif.). DNA was amplified using 30 cycles of 3-min. incubations at 94° C. followed by 61° C. and then by 72° C. To avoid detection of endogenous MDR1 genes, MDR1, primers were derived from different exons (exons 4 and 6), which are assayed by greater than 23 kb of intervening sequence. The amplified fragments were separated by electrophoresis in a 1.4% agarose gel and visualized by ethidium bromide staining, and the size was determined using DNA molecular weight markers (GIBCO BRL, Grand Island, N.Y.).

The effect of centrifugation of vector on target cell transduction was investigated. Nine different retroviral vectors were assayed for their ability to transduce NIH-3T3 TK cells with or without centrifugation. An increase in titer as dertermined by the number of G418-resistant colonies was observed in all experiments. Representative results are shown in Table VII. This method has now been used over 50 times with NIH-3T3 TK cells as the target cell. The titer increases in samples varied from 1 to 18-fold.

Figure 3A:
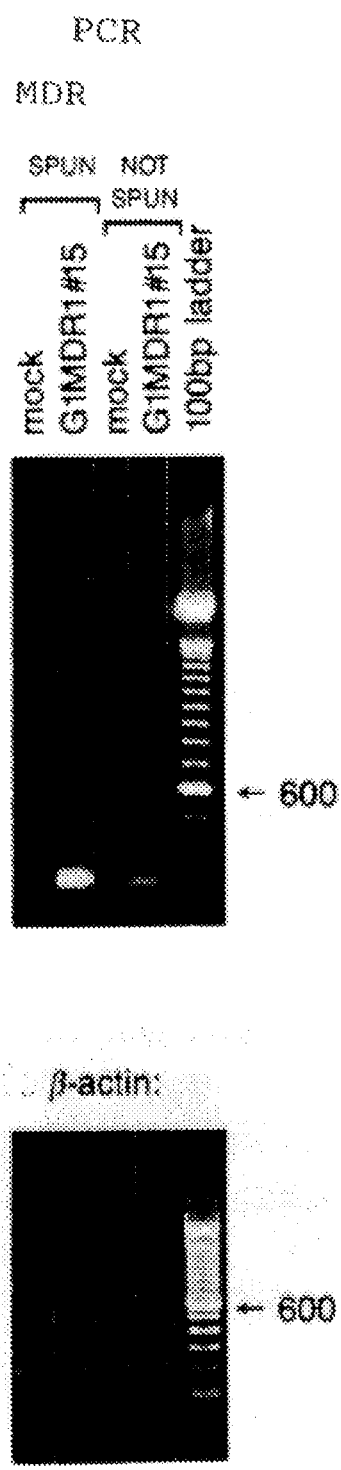
FIG. 3. A total of 1×10$^6$ cells in a 24-well plate were transduced with and without centrifugation (spun) at 2,500 rpm at 32° C. for 90 min. Cells were incubated overnight at 32° C. Three days after transduction the cells were prepared for PCR and FACS analyses. A. PCR agarose gel profile. Ethidium bromide-stained gel of amplification products obtained using primers specific for MDRI(1) or β-actin(2). Products were amplified from 1 µg of genomic DNA isolated from mock-transduced cells or cells transduced with PA317/G1MD1-15. The 100 bp ladder was obtained from GIBCO BRL. B. Flow cytometry (FACS analysis). Cells were harvested and suspended in basal DMEM containing 0.1 µg/ml rhodamine-123. Cells were incubated at 37° C. for 20 min., then centrifuged at 1,500 rpm for 10 min. Cells were resuspended in basal medium and effluxed at 37° C. for 45 min. Flow cytometry was performed by EPICS cytometer (Coulter).
Figure 3B:
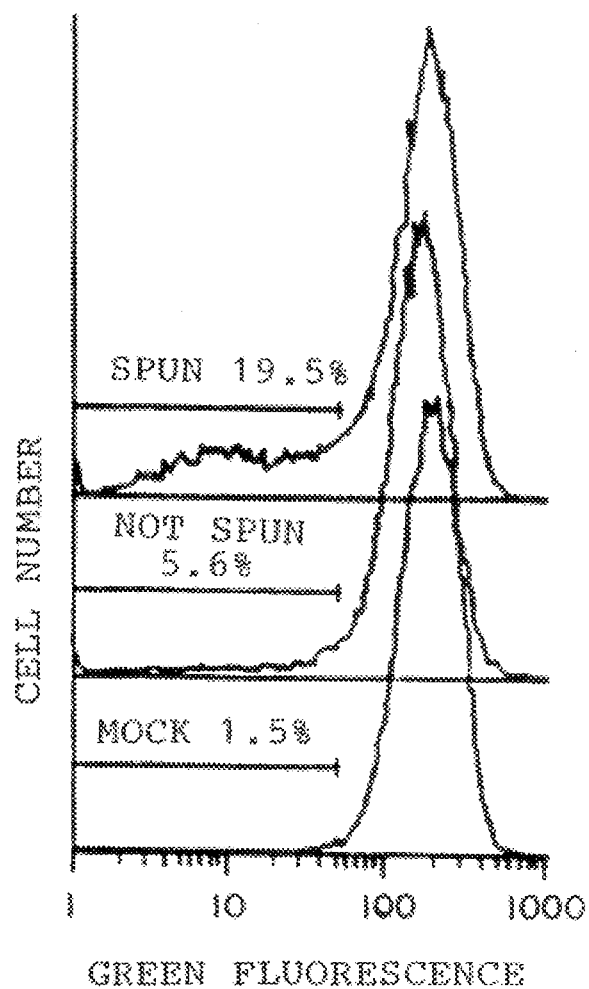

In addition to NIH-3T3 TK cells, a human leukemia line that grows in suspension, HUT 78, was also transduced with and without centrifugation. In this experiment, HUT 78 cells were transduced with amphotropic vector PA317/G1MD.1-15, which can express the broad specificity efflux pump responsible for multidrug resistance (MDR1). FACS analysis shown in FIG. 3B demonstrates that centrifugation (19.5%) yielded approximately three timed more cells capable of rhodamine effluex than were obtained without centrifugation (5.6%). Consistent with this result, amplification of MDR1 sequences in these cells by PCR revealed that cells transduced using centrifugation contained more G1MD proviral sequences than cells transduced without centrifugation (FIG. 3A), directly demonstrating that centrifugation leads to increased transduction efficiency.

TABLE 7

COMPARISON OF VECTOR TRANSDUCTION ON NIH-3T3 TK⁻ CELLS WITH AND WITHOUT CENTRIFUGATION (2,500 rpm, 90 min)

| Culture methods | Producer cells | Vector titer (cfu/ml)ᵃ | | Titer increase |
|---|---|---|---|---|
| | | No centrifugation | Centrifugation | |
| Cell Cube | PA317/G1NaSvAd.24 | $2.0 \times 10^6$ | $2.2 \times 10^7$ | 11× |
| | | $3.4 \times 10^6$ | $2.7 \times 10^7$ | 8× |
| | | $2.6 \times 10^6$ | $2.3 \times 10^7$ | 9× |
| Roller bottle | PA317/G1Na.40 | $2.6 \times 10^7$ | $2 \times 10^8$ | 8× |
| | PA317/G1NaSvAd.24 | $1.7 \times 10^6$ | $1.1 \times 10^7$ | 7× |

TABLE 7-continued

COMPARISON OF VECTOR TRANSDUCTION ON NIH-3T3 TK⁻ CELLS
WITH AND WITHOUT CENTRIFUGATION (2,500 rpm, 90 min)

| Culture methods | Producer cells | Vector titer (cfu/ml)[a] | | Titer increase |
|---|---|---|---|---|
| | | No centrifugation | Centrifugation | |
| | | $1.1 \times 10^6$ | $1.5 \times 10^7$ | 14× |
| | PA317/L1XSN | $5.7 \times 10^5$ | $5.5 \times 10^6$ | 10× |
| | PA317/G1F1SvNa.19c | $6.0 \times 10^5$ | $7.8 \times 10^6$ | 13× |
| | PA317/G1IL2RαSvNa.3 | $1.1 \times 10^6$ | $1 \times 10^7$ | 9× |
| | PA317/G1IL2RβSvNa.4 | $2.0 \times 10^5$ | $3.3 \times 10^6$ | 17× |
| | PA317/G1NaBcl2G.6 | $6.0 \times 10^5$ | $9.5 \times 10^6$ | 16× |
| | PA317/G1T2SvNa.24 | $1.2 \times 10^5$ | $7 \times 10^6$ | 14× |
| T75 | PE501/G1NaBcLa1 | $5 \times 10^5$ | $1.8 \times 10^6$ | 4× |

[a]Titers determined by G418 selection method.

An efficient transduction method is a key component for clinical utilization in clinical trials. Most protocols incorporate a 37° C. incubation tempature for various transduction times. A novel transduction procedure has been developed using the combination of centrifugation and 32° C. overnight incubation. Centrifugation has been used for improved detection of other viruses, and chlamydia in clinical specimens (Ripa and Mardh *Nongonococal Urethritis and Related Infections*, Holmes, et al., eds., American Society for Microbiology, Washington, D.C., pgs. 323–327, 1977; Heggie and Huang, *J. Virol. Methods*, Vol 41, pgs. 1–7, 1993) The combination of centrifugation and overnight transduction of NIH-3T3 TK⁻ cells at 32° C. resulted in a 4- to 18-fold increase compared to the overnight transduction at 32° C. The actual mechanism for the success of this centrifugation method is not well understood; however, aggregation of vector particles and/or vector particles with debris may play a role. The supernatants from roller bottles and cCellCube appeared to be more viscous than supernatant from the 175 flask, although all supernatants were filtered through a 1.2 μm filter. Transduction by centrifugation on human leukemic HUT 78 cells also demonstrated a significant increase in trasnduction efficiency as determined by FACS and PCR analysis. This technique may result in a dramatic impact for successful gene therapy, especially where vector is in limited concentration. Studies of transduction on clinically relevant target cells such as peripheral blood lymphocytes (PBL), tumor infiltrating lymphocytes (TIL), bone marrow cells, and tumor cells are in progress.

H. Results and Discussion

High titer vectors were produced from retroviral vector producer cells in various monolayer culture systems. Vector supernatant is clarified, and the volume of supernatant containing retroviral vectors was reduced 16 to 25 times with vector recovery ranging from 91% to 96% in a Millipore Pellicon tangential flow filtration system. Subsequently, vectors were purified by a two-step procedure including polyethylene glycol (PEG) preciipitation and sucrose gradient centriguation. The vector reocveries were from 100% to 110% by a standard vector titer assay. This suggests that the vector preparations do not contain free gp70 or empty viral particles which compete for virus binding sites with infectious retroviral vectors. The retroviral vectors, upon recovery, may be lyophilized successfully.

In addition, the above example demonstrates a large-scale technology for retroviral vector production, as well as procedures for concentration, purification, and lyophilization of retroviral vectors, whereby one may obtain a purified composition having a high titer of retroviral vectors. This example demonstrates that retroviral vectors for gene therapy can be produced efficiently, concentrated, purified, and stored in scale-up quantities, and subsequently allows one to transduce a variety of target cells with high efficiency.

All publications cited herein are incorporated by reference.

It is to be understood, however, that the scope of the present invention is not to be limited to the specific embodiments described above. The invention may practiced other than as particularly described and still be within the scope of the accompanying claims.

What is claimed is:

1. A method of transducing cells with retroviral vector particles, comprising:
   (a) contacting a suspension of said retroviral vector particles with said cells to form a mixture of said retroviral vector particles and said cells; and
   (b) centrifuging said mixture for a period of time sufficient to permit transduction.

2. The method of claim 1 wherein said mixture is centrifuged for a period of time of from 30 minutes to 3 hours.

3. The method of claim 1 wherein said mixture is centrifuged at from 1,000 to 4,000 rpm.

4. The method of claim 1 wherein said mixture is centrifuged at a temperature of from 15° C. to 37° C.

5. The method of claim 2 wherein said mixture is centrifuged for a period of time of from 1 hour to 2 hours.

6. The method of claim 5 wherein said mixture is centrifuged for a period of time of 90 minutes.

7. The method of claim 3 wherein said mixture is centrifuged at from 2,000 rpm to 3,000 rpm.

8. The method of claim 7 wherein said mixture is centrifuged at 2,500 rpm.

9. The method of claim 4 wherein said mixture is centrifuged at a temperature of from 20° C. to 35° C.

10. The method of claim 9 wherein said mixture is centrifuged at a temperature of about 32° C.

* * * * *